United States Patent
Sloan et al.

(10) Patent No.: US 10,878,529 B2
(45) Date of Patent: Dec. 29, 2020

(54) REGISTRATION METHOD AND APPARATUS

(71) Applicant: Canon Medical Systems Corporation, Otawara (JP)

(72) Inventors: James Sloan, Edinburgh (GB); Owen Anderson, Edinburgh (GB); Keith Goatman, Edinburgh (GB)

(73) Assignee: Canon Medical Systems Corporation, Otawara (JP)

( * ) Notice: Subject to any disclaimer, the term of this patent is extended or adjusted under 35 U.S.C. 154(b) by 130 days.

(21) Appl. No.: 16/206,388

(22) Filed: Nov. 30, 2018

(65) Prior Publication Data

US 2019/0197662 A1 Jun. 27, 2019

Related U.S. Application Data

(60) Provisional application No. 62/609,431, filed on Dec. 22, 2017.

(51) Int. Cl.
*G06T 3/00* (2006.01)
*G06T 7/37* (2017.01)
(Continued)

(52) U.S. Cl.
CPC ......... *G06T 3/0068* (2013.01); *G06N 3/0454* (2013.01); *G06N 3/0472* (2013.01);
(Continued)

(58) Field of Classification Search
CPC ......... G06T 3/0068; G06T 7/37; G06T 7/337; G06T 5/50; G06T 7/50;
(Continued)

(56) References Cited

U.S. PATENT DOCUMENTS

2015/0016728 A1* 1/2015 Parthasarathy ........... G06T 7/33
382/195
2016/0063720 A1 3/2016 Han et al.
(Continued)

FOREIGN PATENT DOCUMENTS

JP 2013-192569 A 9/2013
WO WO 2013/132402 A2 9/2013

OTHER PUBLICATIONS

De Vos, B.D., et al., "End-to-End Unsupervised Deformable Image Registration with a Convolutional Neural Network", Deep Learning in Medical Image Analysis and Multimodal Learning for Clinical Decision Support: Third International Workshop. DLMIA 2017, Held in Conjunction with MICCAI 2017, Quebec City, QC, Canada, Sep. 14, Proceedings, pp. 1-8.

*Primary Examiner* — Christopher M Brandt
(74) *Attorney, Agent, or Firm* — Oblon, McClelland, Maier & Neustadt, L.L.P.

(57) ABSTRACT

An apparatus comprises processing circuitry configured to receive first image data; receive second medical image data; and apply a transformation regressor to perform a registration process to obtain a predicted displacement that is representative of a transformation between the first image data and the second image data; wherein the transformation regressor is trained in combination with a discriminator in an adversarial fashion by repeatedly alternating a transformation regressor training process in which the transformation regressor is trained to predict displacements, and a discriminator training process in which the discriminator is trained to distinguish between predetermined displacements and displacements predicted by the transformation regressor.

8 Claims, 9 Drawing Sheets

(51) Int. Cl.
  *G06T 7/33* (2017.01)
  *G06T 5/50* (2006.01)
  *G06N 5/04* (2006.01)
  *G06T 7/50* (2017.01)
  *G16H 30/40* (2018.01)
  *G06N 3/08* (2006.01)
  *G06N 3/04* (2006.01)

(52) U.S. Cl.
  CPC .............. *G06N 3/08* (2013.01); *G06N 5/04* (2013.01); *G06T 5/50* (2013.01); *G06T 7/337* (2017.01); *G06T 7/37* (2017.01); *G06T 7/50* (2017.01); *G16H 30/40* (2018.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/20081* (2013.01)

(58) Field of Classification Search
  CPC . G06T 2207/20081; G06T 2207/10116; G06T 2207/10132; G06T 2207/10081; G06T 2207/10108; G06T 2207/10088; G06T 2207/10104; G06N 3/0472; G06N 3/0454; G06N 5/04; G06N 3/08; G16H 30/40; G16H 40/63; G16H 50/20
  See application file for complete search history.

(56) References Cited

U.S. PATENT DOCUMENTS

| | | |
|---|---|---|
| 2017/0294010 A1* | 10/2017 | Shen .................... G06K 9/6256 |
| 2018/0336677 A1 | 11/2018 | Sloan et al. |
| 2019/0384047 A1* | 12/2019 | Johnson ............... G06K 9/3233 |

* cited by examiner

REGISTRATION METHOD AND APPARATUS

FIELD

Embodiments described herein relate generally to an apparatus and method for registering image data, for example an apparatus and method for using a neural network to register medical image data.

BACKGROUND

Medical image registration may comprise the alignment of two images to a common space. Medical image registration may be performed on volume data that is representative of, or can be processed to obtain, medical images. Volume data may be aligned to a common space.

Registration may be used, for example, to provide clinicians with easy access to information not present in one image alone. In one example, the images could be images acquired at different times, and the information provided by the registration could be the development of a tumor over time.

Registration may be performed on images acquired using the same modality of acquisition (mono-modality registration) or on images acquired using different modalities of acquisition (multi-modality registration). In a case of multi-modality registration, registration of an image of soft tissue (for example, a magnetic resonance image) and an image of hard tissue (for example, a computed tomography image) may be performed to create a more extensive representation of patient anatomy.

Registering images may allow a direct comparison of the images. For example, anatomical features may occupy corresponding positions in each image once the images have been registered. In some circumstances, further image processing may be performed on images that have been registered (for example, segmentation, subtraction, or image fusion).

In a registration process in which two images are registered, one of the images may be designated as a reference image and the other image may be designated as a floating image. The aim of the registration process may be to obtain a transformation which relates the coordinate system of the floating image to the coordinate system of the reference image. The transformation may be applied to the floating image to align the floating image with the reference image.

Traditional image registration processes may use a measure of how well the two images are aligned, and iteratively apply transformations to one image with the goal of optimizing this measure of alignment. For example, the measure of alignment may comprise a similarity measure. An initial transformation may be applied to the floating image to obtain a value for the measure of alignment. The initial transformation may then be iterated in such a way as to improve the value for the measure of alignment until the value for the measure of alignment is converged.

In some registration methods, the transformation is a rigid transformation comprising rotation, translation and scaling.

In other registration methods, the transformation is a non-rigid transformation comprising deformation, which may include local deformation. The transformation may be represented by a displacement field.

In general, for non-rigid registration, regularization is employed to constrain the transformation space. Such regularization may constrain, for example, the smoothness of the field, or the maximum possible absolute magnitude of the transformation.

If regularization were not employed, it may be the case that non-rigid registration could output a transformation that did not make physical sense, for example a transformation that represents changes in anatomy that are not physically possible. For example, when an intensity driven metric is used, the non-rigid registration may provide an output that simply matches intensities of pixels between one image and another without considering how the pixels represent anatomy (for example, without keeping neighboring pixels together).

BRIEF DESCRIPTION OF THE DRAWINGS

Embodiments are now described, by way of non-limiting example, and are illustrated in the following figures, in which.

DETAILED DESCRIPTION OF THE DRAWINGS

Figure 1:
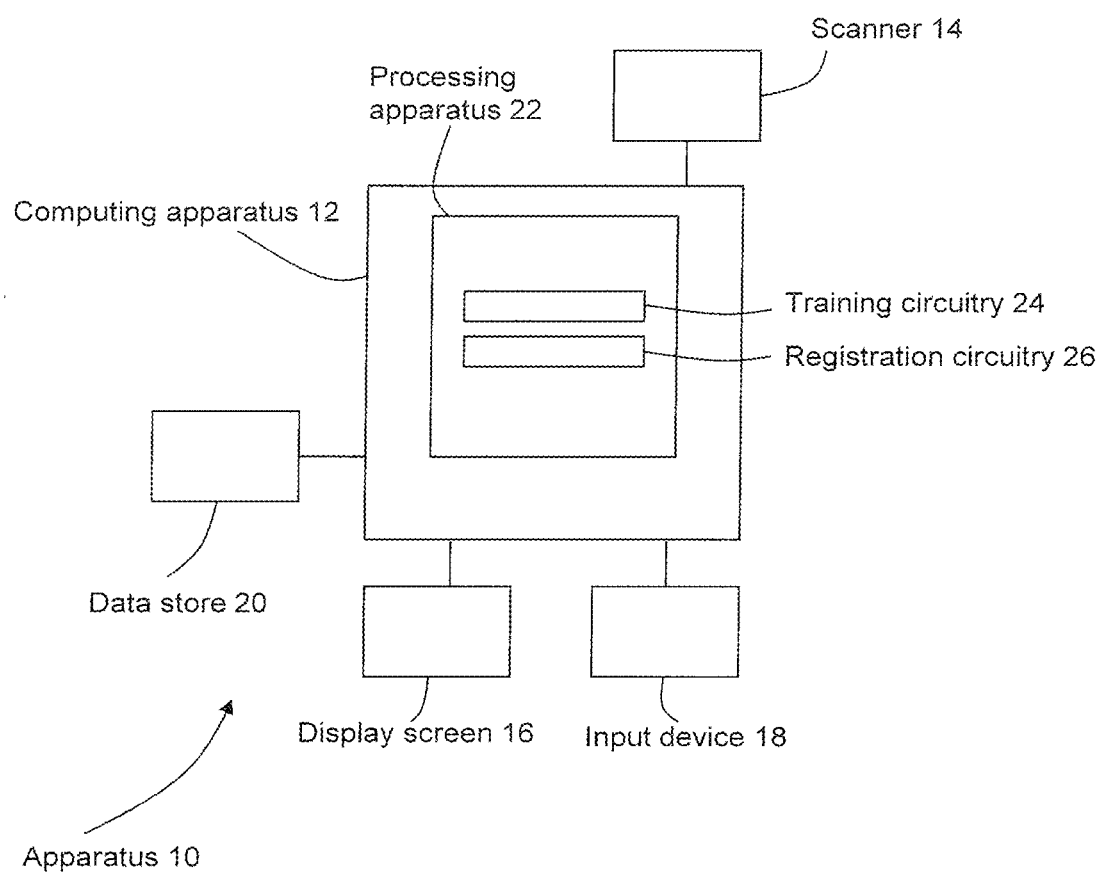
FIG. 1 is a schematic diagram of an apparatus according to an embodiment.

Certain embodiments provide an apparatus comprising processing circuitry configured to: receive first image data; receive second image data; and apply a transformation regressor to perform a registration process to obtain a predicted displacement that is representative of a transformation between the first image data and the second image data; wherein the transformation regressor is trained in combination with a discriminator in an adversarial fashion by repeatedly alternating a transformation regressor training process in which the transformation regressor is trained to predict displacements, and a discriminator training process in which the discriminator is trained to distinguish between predetermined displacements and displacements predicted by the transformation regressor.

Certain embodiments comprise an apparatus comprising processing circuitry configured to: receive a plurality of training image data sets and a plurality of predetermined displacements; and use the training image data sets and predetermined displacements to train a transformation regressor in combination with a discriminator in an adversarial fashion by repeatedly alternating a transformation regressor training process in which the transformation regressor is trained to predict displacements, and a discriminator training process in which the discriminator is trained to distinguish between predetermined displacements and displacements predicted by the transformation regressor.

Certain embodiments provide a method comprising: receiving first image data; receiving second image data; and applying a transformation regressor to perform a registration process to obtain a predicted displacement that is representative of a transformation between the first image data and the second image data; wherein the transformation regressor is trained in combination with a discriminator in an adversarial fashion by repeatedly alternating a transformation regressor training process in which the transformation regressor is trained to predict displacements, and a discriminator training process in which the discriminator is trained to distinguish between predetermined displacements and displacements predicted by the transformation regressor.

Certain embodiments provide a method comprising: receiving a plurality of training image data sets and a plurality of predetermined displacements; and using the training image data sets and predetermined displacements to train a transformation regressor in combination with a discriminator in an adversarial fashion by repeatedly alternating a transformation regressor training process in which the transformation regressor is trained to predict displacements, and a discriminator training process in which the discriminator is trained to distinguish between predetermined displacements and displacements predicted by the transformation regressor.

Certain embodiments provide an apparatus comprising processing circuitry configured to: receive first image data and second image data, wherein the first image data and second image data have been acquired from first and second imaging devices that are offset in position such that the first image data and second image data are representative of a stereo image; and apply a transformation regressor to perform a depth analysis process to obtain a predicted depth field that is representative of a transformation between the first image data and the second image data; wherein the transformation regressor is trained in combination with a discriminator in an adversarial fashion by repeatedly alternating a transformation regressor training process in which the transformation regressor is trained to predict depth fields, and a discriminator training process in which the discriminator is trained to distinguish between predetermined depth fields and depth fields predicted by the transformation regressor.

An image data processing apparatus 10 according to an embodiment is illustrated schematically in FIG. 1. In the embodiment of FIG. 1, the apparatus 10 is configured to train a transformation regressor for registering medical images, and to use the trained transformation regressor to register medical images. In other embodiments, a first apparatus may be used to train the transformation regressor and a second, different apparatus may use the trained transformation regressor to register medical images. In further embodiments, any apparatus or combinations of apparatuses may be used.

The image data processing apparatus 10 comprises a computing apparatus 12, in this case a personal computer (PC) or workstation, which is connected to a scanner 14, one or more display screens 16 and an input device or devices 18, such as a computer keyboard, mouse or trackball.

The scanner 14 may be any scanner that is configured to perform medical imaging. The scanner 14 is configured to generate imaging data that is representative of at least one anatomical region of a patient or other subject. The scanner may be configured to obtain two-dimensional or three-dimensional image data in any imaging modality. For example, the scanner 14 may comprise a magnetic resonance (MR) scanner, CT (computed tomography) scanner, cone-beam CT scanner, X-ray scanner, ultrasound scanner, PET (positron emission tomography) scanner or SPECT (single photon emission computed tomography) scanner. In further embodiments, the scanner may generate any type of image data, which may not be medical imaging data.

In the present embodiment, image data sets obtained by the scanner 14 are stored in data store 20 and subsequently provided to computing apparatus 12. In an alternative embodiment, image data sets are supplied from a remote data store (not shown) which may form part of a Picture Archiving and Communication System (PACS). The data store 20 or remote data store may comprise any suitable form of memory storage.

Computing apparatus 12 comprises a processing apparatus 22 for processing of data, including image data. The processing apparatus comprises a central processing unit (CPU) and Graphical Processing Unit (GPU).

The processing apparatus 22 provides a processing resource for automatically or semi-automatically processing image data sets. For simplicity, we will refer below to the processing of medical images. However, in practice, the operations described below may be performed on any suitable sets of image data that are representative of medical images. Image data may be processed internally by the processing apparatus 22 without any corresponding image being displayed.

The processing apparatus 22 includes training circuitry 24 configured to train a transformation regressor to register medical images and registration circuitry 26 configured to use the trained transformation regressor to register medical images.

In the present embodiment, the circuitries 24, 26 are each implemented in the CPU and/or GPU by means of a computer program having computer-readable instructions that are executable to perform the method of the embodiment. In other embodiments, the various circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
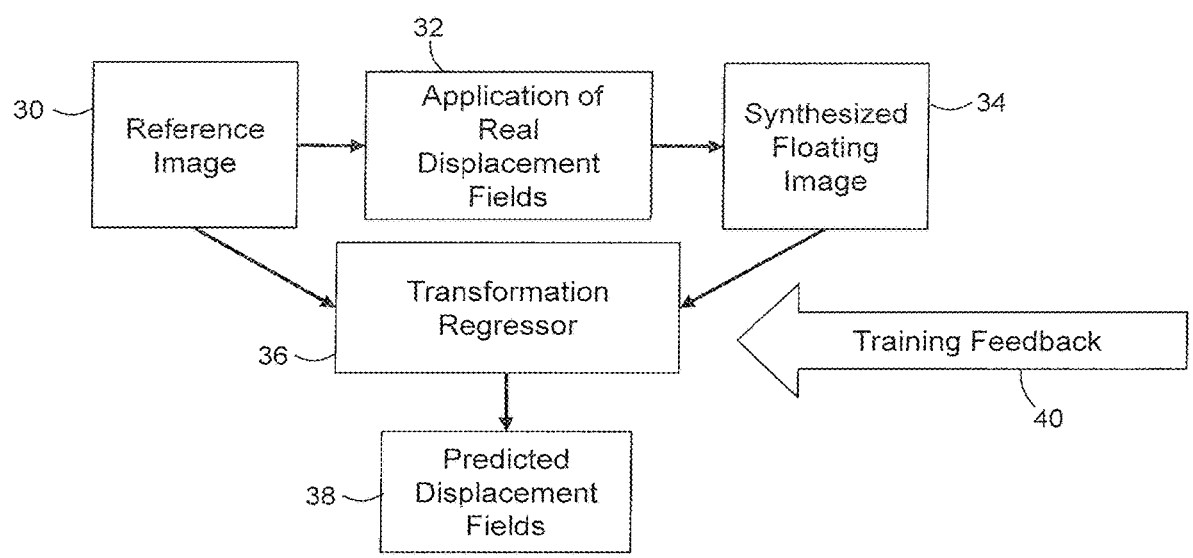
FIG. 2 is a flow chart illustrating in overview a method of training a transformation regressor.

FIG. 2 is a flow chart illustrating in overview a method of training a transformation regressor 36.

The transformation regressor 36 is a neural network which is configured to learn to predict the non-rigid transformation to align two given images. The non-rigid transformation is described by a displacement field. A transformation regressor may comprise any function (for example, any deep learning method) that provides a fitting between two data sets related by a transformation such as to minimize or reduce at least one parameter characterizing the transformation.

A plurality of training images are used to train the transformation regressor 36.

The transformation regressor 36 is trained on ground truth transformations. Ground truth transformations are transformations that are already known. Ground truth transformations may also be described as training transformations or predetermined transformations.

In practice, it may be difficult to obtain transformations for real pairs of images (for example, images of the same anatomy acquired at different points of time) that can be used as ground truth.

Therefore, in the method of FIG. 2, the ground truth transformations are predetermined transformations which have been artificially constructed. For example, the ground truth transformations may be obtained by sampling a 2D Gaussian profile function or by sampling a sinusoidal function. These ground truth transformations are applied to training images to obtain synthesized floating images.

Turning to the flow chart of FIG. 2, a reference image 30 is received. The reference image 30 is one of the training images on which the transformation regressor is to be trained.

At stage 32 of FIG. 2, a predetermined displacement field is applied to the reference image 30. The predetermined field is an artificially constructed displacement field. For example, the predetermined displacement field may have been obtained by sampling a 2D Gaussian function. The predetermined displacement field may also be referred to as a synthetic displacement field, because it is artificially constructed rather than, for example, being obtained by performing a registration process.

The result of applying the predetermined displacement field to the reference image 30 is a floating image 34. The floating image 34 may be referred to as a synthesized floating image, because it has not been acquired from a scanner, but has instead been obtained using the (artificially constructed) predetermined displacement field.

The training circuitry provides the reference image 30 and the synthetic floating image 34 (but not the predetermined displacement field) to the transformation regressor 36.

The transformation regressor 36 is a neural network. The transformation regressor 36 may be initialized with an initial set of weights. Training the transformation regressor 36 may comprise adjusting the weights of the transformation regressor 36.

The transformation regressor 36 uses the reference image 30 and synthetic floating image 34 as inputs to its neural network. The neural network processes the reference image 30 and synthetic floating image 34. For example, the neural network may extract features from the reference image 30 and synthetic floating image 34 and process the extracted features. The neural network outputs a prediction of a displacement field 38 which is representative of a transformation between the reference image 30 and the synthetic floating image 34.

The training circuitry compares the predicted displacement field 38 to the predetermined displacement field that was used at stage 32 to synthesize the floating image 34.

It is known that the predetermined displacement field is the correct transformation between the reference image 30 and the synthesized floating image 34, because the predetermined displacement field was used to construct the synthesized floating image 34. The predetermined displacement field therefore provides a ground truth against which the transformation regressor's prediction is compared.

A measure of difference between the predicted displacement field 38 and the predetermined displacement field is calculated. In the method of FIG. 2, the measure of difference is mean squared error (MSE). In other versions of the method, any suitable measure of difference may be used.

If the prediction provided by the transformation regressor 36 is good, the predicted displacement field 38 will be very similar to the predetermined displacement field. If the prediction provided by the transformation regressor 36 is poor, the predicted displacement field 38 will differ significantly from the predetermined displacement field.

The mean squared error is fed into the transformation regressor 36 as training feedback 40. The training circuitry may update the weights of the transformation regressor 36 in response to the training feedback 40.

The method of FIG. 2 is repeated many times for many different reference images and predetermined displacement fields. The transformation regressor 36 learns from the many instances of training feedback 40 to improve its prediction of displacement fields. The transformation regressor 36 is trained iteratively to minimize the mean squared error between predicted and real displacement fields.

It has been found that in some circumstances optimizing the displacement fields based on mean squared error alone (for example, as described above with reference to FIG. 2) may lead to poor predicted displacements. In some circumstances, small, subtle displacements may be overwhelmed by larger errors elsewhere in the image.

When training a transformation regressor 36 to minimize the mean squared error alone, there are no bounds placed on the shape of the displacement fields it will predict. The transformation regressor 36 may generate displacement fields which are considered to be accurate in terms of the mean squared error, but are unrealistic. The transformation regressor 36 may generate displacement fields which are considered to be accurate in terms of the mean squared error, but are discontinuous. In some circumstances, a predicted displacement field that is output by the transformation regressor 36 may represent a transformation that is not physically possible for the anatomy represented in the images that it is attempting to register.

It may be considered that the solutions provided by training the transformation regressor 36 to minimize the mean squared error alone (for example, as illustrated in FIG. 2) are insufficiently regularized. To overcome the insufficient regularization, it is proposed to add a discriminator to the process of training a transformation regressor. The discriminator may be considered to provide an implicit regularization.

Figure 3:
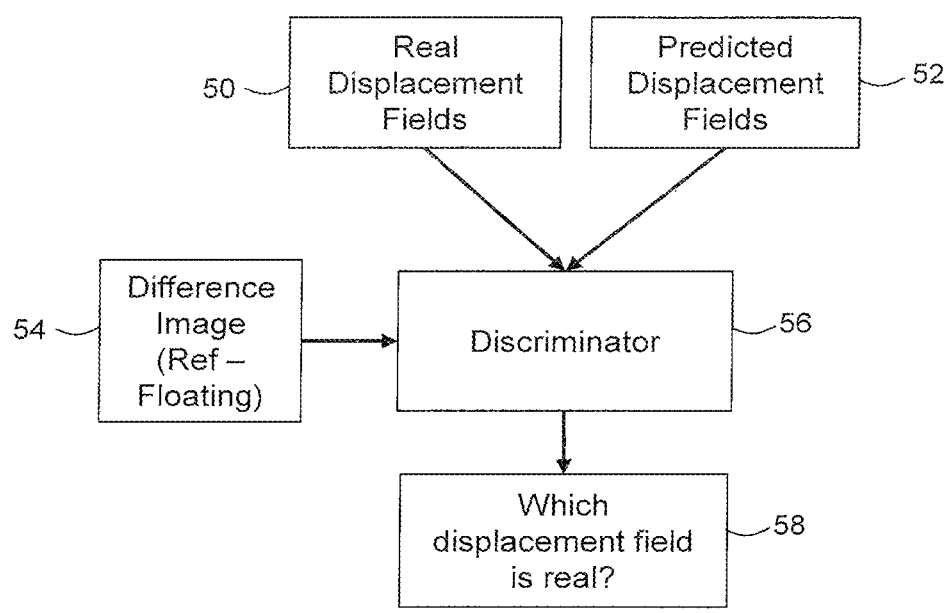
FIG. 3 is a flow chart illustrating in overview a discriminator.

FIG. 3 is a flow chart illustrating in overview a process performed by a discriminator 56. The discriminator is trained to distinguish between real displacement fields 50 (for example, predetermined displacement fields as described above) and predicted displacement fields 52, for example displacement fields that have been predicted by transformation regressor 36.

The discriminator 56 receives two displacement fields 50, 52. One of the two displacement fields is a real displacement field 50 that is representative of a transformation between a reference image and a floating image. For example, the real displacement field 50 may be a predetermined displacement field as described above.

The other of the two displacement fields is a displacement field 52 that has been predicted by a transformation regressor for the same reference image and floating image.

The discriminator 56 is not told which of the two displacement fields 50, 52 is real and which is predicted.

In the example of FIG. 3, the discriminator 56 also receives a difference image 54. The difference image 54 is obtained by subtracting the floating image from the reference image.

The discriminator 56 processes the displacement fields and the difference image. In the example of FIG. 3, the discriminator comprises a neural network. The neural network receives as inputs the predetermined displacement field 50, the predicted displacement field 52, and the difference image 54. The neural network processes the inputs 50, 52, 54. For example, the neural network may extract features from the displacement fields and the difference image and process the extracted features.

The neural network outputs a determination of which of the two displacement fields 50. 52 it judges to be real, and which it judges to be predicted. The determination may comprise a classification of one of the displacement fields 50, 52 as real and a classification of the other of the displacement fields 50, 52 as predicted. The determination may comprise, for each displacement field 50, 52, a probability or likelihood that the displacement field is real. The determination may comprise, for each displacement field 50, 52, a probability or likelihood that the displacement field 50, 52 is predicted.

Figure 4A:
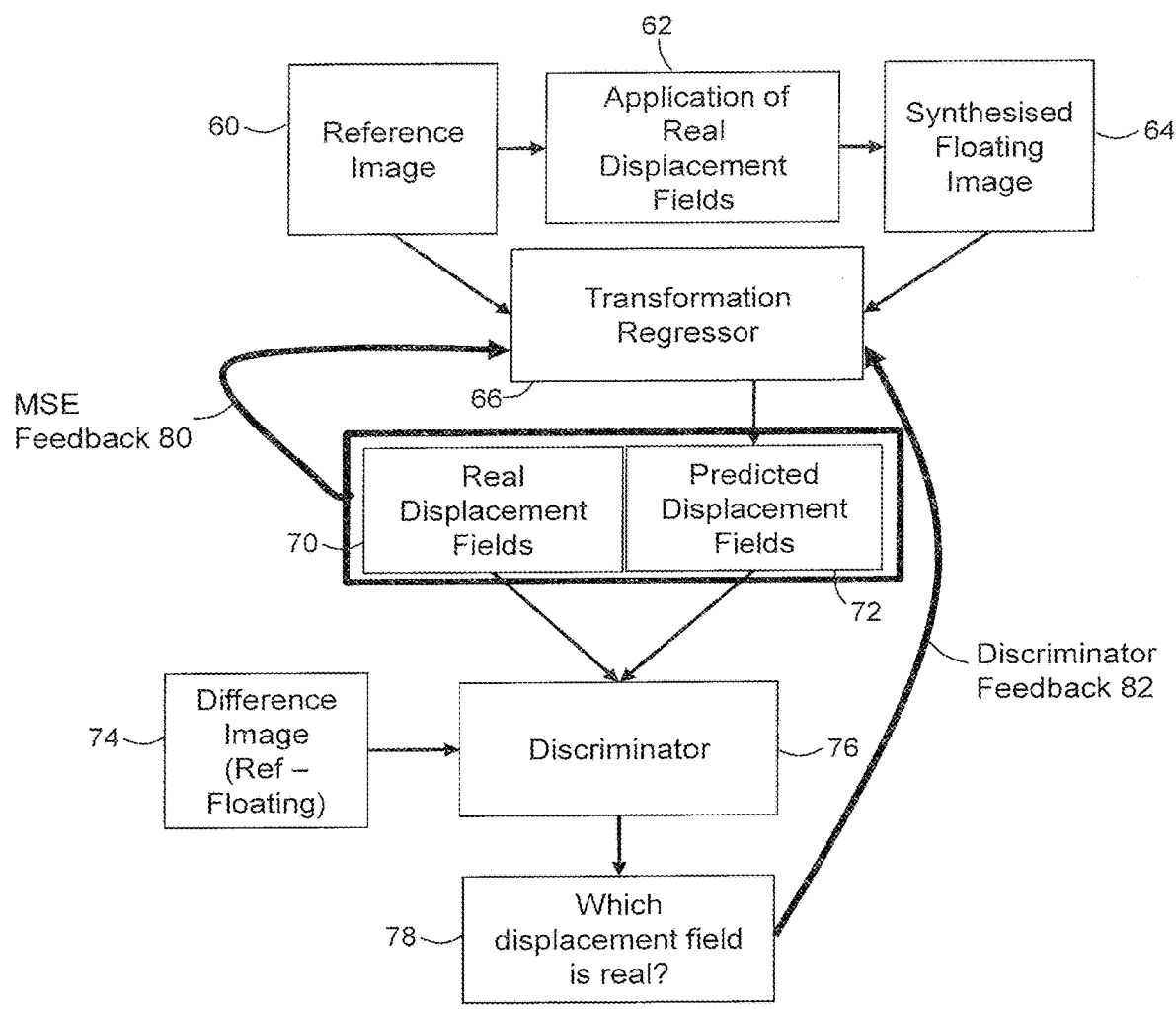
FIG. 4a is a flow chart illustrating in overview a method of training a transformation regressor in accordance with an embodiment.
Figure 4B:
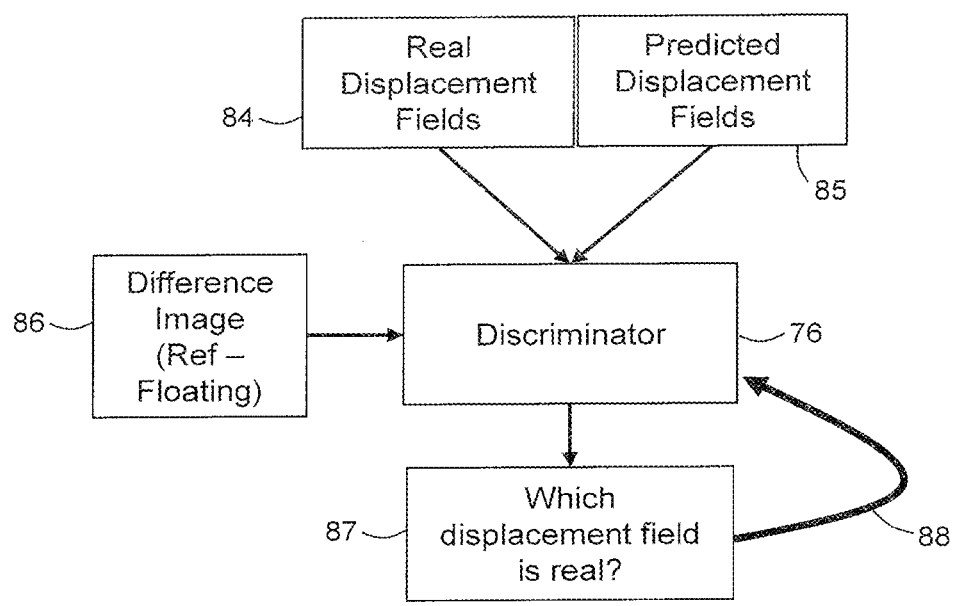
FIG. 4b is a flow chart illustrating in overview a method of training a discriminator in accordance with an embodiment.

FIGS. 4a and 4b are flow charts illustrating in overview a method of training a transformation regressor 66 in accordance with an embodiment. The training of the transformation regressor 66 is performed by the training circuitry 24 of the apparatus of FIG. 1.

To train the transformation regressor 66, the training circuitry 24 uses an adversarial network, which may be referred to as a deterministic adversarial network (DAN). The deterministic adversarial network comprises two parts. A first part of the deterministic adversarial network is the transformation regressor 66. The transformation regressor 66 comprises a first deep neural network. A second part of the deterministic adversarial network is a discriminator 76. The discriminator 76 comprises a second deep neural network.

A deep neural network may be a neural network that comprises stacked layers of neurons. The stacked layers of neurons may have non-linear activation functions that use the output of one or more previous layers as a subsequent layer's input. Deep neural networks may construct highly non-linear mappings from an input space to an output space, and may thereby capture complex relationships of a process or task that is to be modelled.

In the embodiment of FIGS. 4a and 4b, each of the transformation regressor 66 and the discriminator 76 comprises a respective convolutional neural network. In other embodiments, any suitable type of deep neural network may be used, for example a multi-layer perceptron, a convolutional neural network with skip connections, a recurrent neural network. In further embodiments, the discriminator 76 comprises an algorithm that does not comprise deep learning.

The transformation regressor 66 and the discriminator 76 are trained repeatedly in an adversarial fashion. The training circuitry 24 alternates between training the transformation regressor 66 and training the discriminator 76 on a batch-wise basis. The adversarial training alternates between a transformation regressor training stage and a discriminator training stage. The transformation regressor training stage is described below with reference to FIG. 4a. The discriminator training stage is described below with reference to FIG. 4b.

In the transformation regressor training stage, the transformation regressor 66 is trained (which may comprise, for example, updating weights of the transformation regressor 66) and the discriminator 76 is kept constant. In the discriminator training stage, the discriminator 76 is trained (which may comprise, for example, updating weights of the discriminator 76) and the transformation regressor 66 is kept constant.

The discriminator 76 is trained to discriminate between predetermined displacement fields and displacement fields 66 that have been predicted by the transformation regressor. The transformation regressor 66 is trained to produce displacement fields that are similar enough to the predetermined displacement fields to fool the discriminator 76. By alternating optimization of the transformation regressor 66 with optimization of the discriminator 76, the transformation regressor 66 gets better at producing displacement fields, and the discriminator 76 gets better at distinguishing between predetermined and predicted displacement fields. By training the transformation regressor 66 and discriminator 76 together in an adversarial fashion, better displacement fields may be produced than if the transformation regressor 66 were to be trained alone. In particular, the displacement fields may be better regularized than if the transformation regressor 66 were to be trained alone. The displacement fields may be less likely to exhibit unrealistic behavior. The displacement fields may be less likely to exhibit discontinuities.

Training deep neural networks in an adversarial fashion is discussed further in Goodfellow et al, Generative Adversarial Nets, NIPS'14 Proceedings of the 27th International Conference on Neural Information Processing Systems, pages 2672-2680, which is hereby incorporated by reference.

A pre-training process (not shown) may be performed by the training circuitry 24 to initialize weights of the transformation regressor 66 and/or the discriminator 76. For example, the transformation regressor 66 may be pre-trained using the method of FIG. 2 which uses solely the mean squared error as the objective function, and the resulting transformation regressor 66 may be used as an initial model for adversarial training.

FIG. 4a illustrates the transformation regressor training stage, which is the part of the adversarial training process in which the training circuitry 24 trains the transformation regressor 66 while the discriminator 76 is kept constant.

The transformation regressor training stage comprises determining a set of weights for the deep neural network of the transformation regressor 66, which in this embodiment is a convolutional neural network. The training process trains the transformation regressor 66 using the discriminator 76. While training the transformation regressor 66, the weights of the discriminator 76 are frozen so that only the weights of the transformation regressor 66 are updated.

The training process shown in FIG. 4a starts with a training image, shown as reference image 60. Although only one training image (reference image 60) is shown in the flow chart of FIG. 4a, in practice the training process of FIG. 4a is performed on a large number of training images, for example hundreds or thousands of training images. The training images are medical images acquired using the scanner 14. The training images may be acquired using any suitable imaging modality.

The reference image 60 is received by the training circuitry 24 from the data store 20. In other embodiments, the reference image 60 may be received from any suitable data store, or from the scanner directly.

At stage 62 of FIG. 4a, the training circuitry 24 applies a predetermined displacement to the reference image. In the present embodiment, the predetermined displacement is a displacement field 70 that is representative of a non-rigid transformation. In other embodiments any displacement may be used. Any suitable format or function of displacement may be used to represent the transformation.

In the present embodiment, the transformation is non-parameterized. In other embodiments, the transformation may be parameterized. In the embodiment of FIG. 4a, the predetermined displacement field has been obtained by sampling a 2D Gaussian profile.

Although only one synthetic displacement field 70 is shown in FIG. 4b, in practice the training process of FIG. 4a is performed on a large number of synthetic displacement fields, for example hundreds or thousands of synthetic displacement fields. In the present embodiment, the synthetic displacements are sampled from a 2D Gaussian profile function of the form:

$$G(x, y) = \frac{A}{N}\exp\left\{\frac{(x-c_x+u_x)^2}{\sigma_x^2} + \frac{(y-c_y+u_y)^2}{\sigma_y^2}\right\}$$

where A is a real number, uniformly drawn from U(−6.5, 6.5), N is a normalisation constant such that $$\max\left\{\frac{1}{N}\exp\left(\frac{(x-c_x+u_x)^2}{\sigma_x^2} + \frac{(y-c_y+u_y)^2}{\sigma_y^2}\right)\right\} = 1,$$

$\sigma_x^2 = \sigma_y^2 = 15$, $c_x = c_y = 128$ such that the Gaussian is shifted from the center of the image by $u_x$ and $u_y$ which are real numbers drawn independently from U(−55,55). To construct a displacement field D={$D_x,D_y$} to synthesize a floating image from the reference image, a Gaussian profile is sampled independently from the above equation for $D_x$ and $D_y$.

In other embodiments, any suitable manner of obtaining the predetermined displacement field 70 may be used. For example, any model may be used that makes the predetermined displacement field 70 resemble displacement fields that arise from real physical deformations.

The predetermined displacement field 70 deforms the reference image 60 to obtain a synthesized floating image 64.

The training circuitry 24 subtracts the synthesized floating image 64 from the reference image 60 to obtain a difference image 74.

The reference image 60, floating image 64, displacement field 70 and difference image 74 may together be considered to provide a set of training data for training the transformation regressor 66.

In other embodiments, the reference image 60 is pre-processed using the displacement field 70 to obtain a floating image 64 and difference image 74 before the training process starts. In further embodiments, a reference image, floating image, displacement field and different image may be obtained in any suitable manner. For example, in some embodiments, the predetermined displacement field 70 may be obtained by applying any suitable registration process to a reference image and floating image.

The training circuitry 24 provides the reference image 60 and floating image 64 to the transformation regressor 66. The transformation regressor 66 uses the reference image 60 and floating image 64 as inputs to its neural network. Given the reference image 60 and floating image 64, the transformation regressor 66 predicts the displacement field, in a non-parametric formulation, to align the two given images.

The neural network of the transformation regressor 66 outputs a predicted displacement field 72.

In the present embodiment, the predicted displacement field 72 is representative of a non-parametric transformation (for example, a dense warp field). In other embodiments, the predicted displacement field may be representative of a parametric transformation. For example, the parametric transformation may comprise spline coefficients for a single-scale or multi-scale grid of control points for the transformation. In further embodiments, a displacement may be represented by any suitable representation. For example, a displacement may be represented as a field or as a parameterized equation.

The training circuitry 24 provides the predetermined displacement field 70 and the predicted displacement field 72 to the discriminator 76. The training circuitry 24 does not indicate to the discriminator 76 which of the displacement fields 70, 72 provided is predetermined and which is predicted. In the present embodiment, the training circuitry 24 also provides the difference image 74 to the discriminator 76. In other embodiments, the training circuitry 24 may provide to the discriminator 76 the reference image and/or floating image. The training circuitry 24 may provide to the discriminator 76 any image or data derived from the reference image 60 and/or floating image 64. For example, the training circuitry 24 may provide to the discriminator 76 a distance function obtained from the reference image 60 and floating image 64. The training circuitry 24 may provide to the discriminator 76 a similarity measure obtained from the reference image 60 and floating image 64. The training circuitry 24 may provide to the discriminator 76 any form of a residual image between the reference image and floating image, for example the square of the dot product between the gradients of the reference and floating images.

The discriminator 76 uses the predetermined displacement field 70 and the predicted displacement field 72 as inputs to its neural network. The neural network of the discriminator 76 outputs a determination 78 of which of the displacement fields it judges to be predetermined and which it judges to be predicted. The determination 78 comprises or represents a classification of each of the displacement fields 70, 72. In the present embodiment, the determination comprises a probability related to which of the two supplied displacement fields is the predetermined displacement field.

In other embodiments, the determination may comprise any suitable classification. The classification may comprise a binary classification of each displacement field as predetermined or predicted. The classification may comprise a probabilistic classification comprising a probability or likelihood that each image is predetermined or predicted.

The training circuitry 24 provides feedback to the transformation regressor 66. The feedback comprises a first component based on the output of the transformation regressor 66 and a second component based on the output of the discriminator 76. The first component 66 is shown in FIG. 4 as MSE feedback 80. The second component is shown in FIG. 4 as discriminator feedback 82.

The training circuitry 24 adjusts weights of the transformation regressor 66 in response to the two components 80, 82 of the feedback.

In the present embodiment, the MSE feedback 80 is a value for an objective function, which may be referred to as a loss function or as a traditional loss function. The objective function provides a measure of the difference between the predicted displacement field 72 and the predetermined displacement field 70.

It is known that the predetermined displacement field 70 correctly represents the transformation between the reference image 60 and the floating image 64, since the predetermined displacement field 72 was used to construct the floating image 64. Therefore, the predetermined displacement field 72 acts as a ground truth, and an error in the predicted displacement field is quantified by comparing the predicted displacement field 72 to the predetermined displacement field 70.

In the present embodiment, the objective function is the mean squared error objective. In other embodiments, any objective function may be used, for example Mean Absolute Error or Huber loss. The objective function may be based on comparison of displacement fields or on comparing the reference and floating images directly.

In the present embodiment, the objective function is a traditional loss function that is suitable for registering images of the same modality (mono-modality registration), for example the mean squared error between images. In other embodiments, if the intended use case of the transformation regressor is to register images of different modalities (multi-modality registration), a loss function that is suitable for multi-modality registration may be used. For example, the calculation of a mean squared error between displacement fields may be used, which is independent of modality. In some embodiments, the traditional loss function is based on an image residual that is suitable for multi-modality registration, for example normalized gradient fields.

In the present embodiment, the objective function is computed directly between the predicted displacement field, which may be denoted as $D^{pred}$, and the predetermined displacement field, which may be denoted as $D^{groundtruth}$. For example, the value calculated may be written as $(D^{pred} - D^{groundtruth})^2$.

In other embodiments, the objective function may be computed in any suitable manner. In some embodiments, the predicted displacement field is applied to the floating image to obtain a transformed floating image, which may also be referred to as a corrected floating image. The objective function is computed between the reference image and the transformed floating image. The reference image may be denoted as R. The transformed floating image may be written as $F \circ D^{pred}$, where F is the floating image and $\circ$ is the transformation operation using the predicted displacement field. The objective function may be computed as $(R - F \circ D^{pred})^2$. If an objective function using a reference image and transformed floating image is used, it may be the case that ground truth displacements do not need to be used. In such cases, ground truth displacements may not be provided to the discriminator.

The discriminator feedback 82 is a value for a further function, which may be described as a discriminatory loss function. The discriminatory loss function represents the error of the discriminator 76 in detecting which of the displacement fields provided to it is predetermined and which is predicted. Any suitable function may be used for the discriminatory loss function. For example, the discriminatory loss function may comprise a binary cross entropy.

The training circuitry 24 adjusts the weights of the transformation regressor 66 to minimize the mean squared error between the output of the transformation regressor and the predetermined displacement fields, and to maximize the error of the discriminator 76. Since the transformation regressor 66 is actively being trained to trick the discriminator 76 into believing that the predicted displacement field is real, weights within the transformation regressor 66 are adjusted whilst training to maximize the error signal of the discriminator 76.

The relative contributions of the MSE feedback 80 and the discriminator feedback 82 may be different in different embodiments. In particular, different levels (which may also be described as strengths) of the discriminator feedback 82 may be used. It may be said that the level of discriminator feedback used may affect how regularized the resulting displacement fields are. In a hypothetical scenario in which only the discriminator were used to train the transformation regressor, the displacement fields produced by the transformation regressor may be highly realistic (for example, highly continuous) but may not relate to the reference and floating image. By using the MSE feedback 80 and the discriminator feedback 82 in combination, displacement fields may be found that relate the reference image to the floating image while also being regularized.

A balance between the MSE feedback 80 and the discriminator feedback 82 may be found by tuning. In some embodiments, the tuning is based on manual inspection of the predicted transformations. In some embodiments, the tuning is based on measuring one or more characteristics of the displacement fields. For example, the one or more characteristics may comprise whether the predicted displacement fields are locally invertible, which may be measured by calculating the determinant of the Jacobian of the predicted displacement fields.

The process of FIG. 4a is repeated for a plurality of training images to train the weights of the transformation regressor 66.

The transformation regressor training stage described above with reference to FIG. 4a is alternated with a discriminator training stage. FIG. 4b is a flow chart illustrating in overview the discriminator training stage.

In the discriminator training stage, the training circuitry 24 trains the discriminator 76 using a plurality of predetermined displacement fields and a corresponding plurality of predicted displacement fields. The predicted displacement fields have been predicted by the transformation regressor 66. To produce the predicted displacement fields on which the discriminator is to be trained, the weights of the transformation regressor 66 are fixed.

Turning to FIG. 4b, the training circuitry 24 receives a predetermined displacement field 84, a predicted displacement field 85, and a difference image 86. The training circuitry 24 provides the predetermined displacement field 84, predicted displacement field 85 and difference image 86 to the discriminator 76. Although only a single predetermined displacement field 84, predicted displacement field 85, and difference image 86 are illustrated in FIG. 4b, in practice the method of FIG. 4b may be performed on a large number of pairs of displacement fields, for example hundreds or thousands of pairs.

The difference image 86 is a difference between a reference image and a floating image that are related by the predetermined displacement field 84. For example, the floating image may have been created from the reference image using the predetermined displacement field 84 as described above. The predicted displacement field 85 has been predicted by the transformation regressor 66 from the same reference image and floating image.

The discriminator 76 uses the predetermined displacement field 84, predicted displacement field 85, and difference image 86 as inputs to its neural network. The discriminator 76 attempts to determine which of the displacement fields 84, 85 is the predetermined displacement field and which is the predicted displacement field. In the present embodiment, the discriminator 76 generates a probability related to which of the two supplied displacement fields 84, 85 is the predetermined displacement field.

The training circuitry 24 computes an error signal of the discriminator 76. The error signal of the discriminator 76 is representative of the degree of success with which the discriminator 76 discriminates between the predetermined displacement field 84 and predicted displacement field 85.

In the present embodiment, the error signal used to train the discriminator 76 is the same discriminatory loss function as was described above with relation to FIG. 4. In other embodiments, a different function may be used.

The training circuitry 24 provides the value for the discriminatory loss function to the discriminator as discriminator feedback 88. The training circuitry 24 adjusts the weights of the discriminator 76 to minimize the discriminatory loss function.

The discriminator training stage is performed for a plurality of predetermined and predicted displacement fields.

The transformation regressor training stage and discriminator training stage are alternated until convergence is reached.

In the present embodiment, the number of training examples used in each transformation regressor training stage and the number of training examples used in each discriminator training stage is a fixed number. It has been found that the use of a fixed number of training examples before switching between transformation regressor training and discriminator training may result in a stable training of the system. In other embodiments, different numbers of training examples may be used in different training stages.

The number of training examples used may be referred to as a switch rate. In some embodiments, tuning of the switch rate is automated based on monitoring one or more characteristics of loss with training. For example, the training circuitry 24 may switch from training the discriminator to training the transformation regressor once the loss value for the discriminator has dropped below a predetermined value (or vice versa).

In the present embodiment, training of the system is stopped when the transformation regressor begins to overfit to the training data. This is measured by retaining a subset of data as validation data which is not used to train the system. The value of the loss function is periodically calculated on the validation data as the training progresses. When the value of the loss function no longer decreases as training progresses, the training is stopped.

In summary, the transformation regressor 66 is trained using predetermined transformations. The predetermined transformations are non-rigid transformations and are described using displacement fields. The training of the transformation regressor 66 uses a discriminator 76. The discriminator 76 is a type of deep neural network which is trained to recognize the characteristics of a realistic displacement field. The discriminator 76 provides additional feedback to help train the transformation regressor, allowing it to predict displacement fields which are still accurate (MSE feedback) but better regularized (discriminator feedback).

After the training, the discriminator 76 is removed from the system, leaving the transformation regressor 66. The trained transformation regressor 66 may then be used to register new images for which a transformation between the images is not yet known.

Figure 5:
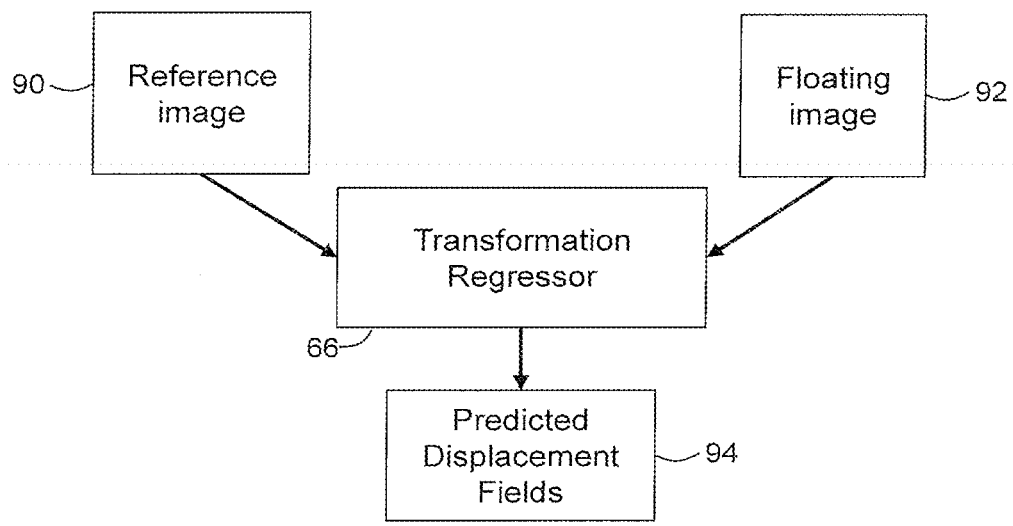
FIG. 5 is a flow chart illustrating in overview the deployment of a trained transformation regressor in accordance with an embodiment.

FIG. 5 is a flow chart illustrating in overview the use of the trained transformation regressor 66.

The registration circuitry 26 receives two medical images 90, 92 that are to be registered to each other. The two medical images may be referred to as a reference image 90 and a floating image 92. In some embodiments, the medical images 90, 92 may be images of the same anatomy of the same patient, for example images of the same anatomy that have acquired at different times. In some embodiments, the medical images 90, 92 may be images of different subjects. In some embodiments, one of the medical images 90 may comprise or form part of an anatomical atlas.

The registration circuitry 26 provides the reference image 90 and floating image 92 as inputs to the transformation regressor 66. The neural network of the transformation regressor 66 has been trained to output a predicted displacement field. The process performed by the trained transformation regressor 66 may be described as a registration process.

The transformation regressor 66 outputs a predicted displacement field 94 which is representative of a transformation between the reference image 90 and floating image 92. The predicted displacement field may be applied to align the reference image 90 and floating image 94.

The processing circuitry 22 may make use of the displacement field 94 and/or the aligned images to perform a further process. The further process may be any process for which registration of images is a prerequisite. For example, the further process may comprise a further registration. The further process may comprise a segmentation. The further process may comprise detection of at least one anatomical feature in the images. The further process may comprise detection of at least one pathology in the images, for example detection of a lesion in the image. In some embodiments, the detection of the anatomical feature and/or pathology may comprise segmentation. In other embodiments, the detection of the anatomical feature and/or pathology may comprise detection of the presence of the anatomical feature and/or pathology. In other embodiments, the detection of the anatomical feature and/or pathology may comprise determining a location (for example, a single coordinate) for the anatomical feature and/or pathology. In some embodiments, the transformation regressor 66 is used to register images to an atlas to perform atlas-based segmentation or another atlas-based process.

The further process may comprise a subtraction or other Boolean operation. The further process may comprise an image fusion in which features of the aligned images are combined to form a single image.

In the embodiment described above with reference to FIG. 4a, FIG. 4b and FIG. 5, deep learning models are used to regress non-rigid transformations to align two images.

Since the neural network of the transformation regressor 66 has been trained to produce displacement fields, the transformation regressor 66 produces a predicted displacement field in one step. Producing a predicted displacement field in one step is different from some known registration methods that use many iterations of a registration process to perform a registration. By using a trained neural network, a registration may be obtained more quickly than with some known registration methods.

The transformation regressor 66 is a single-pass transformation regressor configured to predict non-rigid displacement fields between images. The trained transformation regressor 66 may provide a registration method that is fast and non-iterative.

The transformation regressor 66 will have learned to produce displacement fields which not only minimize the mean squared error but also fool the discriminator that has been present during training. Since it is trained to fool the discriminator, it may be expected that the trained transformation regressor will output realistic displacement fields.

Using a deterministic adversarial network to train a transformation regressor can be thought of as additional regularization of the solution displacement fields as the transformation regression trains. The discriminator can be thought of as an additional regularizer during training of the transformation regressor, as it constrains the displacement fields that the transformation regressor predicts by penalizing displacement solutions that it predicts are fake.

Training the transformation regressor 66 and the discriminator 76 in an adversarial fashion may produce a better transformation regressor 66 than if the transformation regressor 66 were to be trained alone without using the output from the discriminator 76.

The displacement fields produced by the transformation regressor 66 may be better regularized. The discriminator 76 implicitly regularizes the predicted transformation/displacement fields learned by the transformation regressor 66. The discriminator 76 provides another form of feedback to help train the transformation regressor 66. The discriminator 76 takes three inputs: the true and predicted displacement fields, and a difference image. The discriminator 76 generates a probability related to which of the two supplied fields is the true displacement field. The transformation regressor 66 is trained with the goal of tricking the discriminator 76, and in addition minimizing the difference between the real and predicted displacement fields.

In the present embodiment, the adversarial training of the transformation regressor 66 is performed using whole images, and the trained transformation regressor 66 uses whole images as its inputs. In other embodiments the training and/or use of the transformation regressor 66 may be performed patch-wise on parts of images, instead of at the whole image level. In a patch-wise method, images or image volumes are divided into sub-images or sub-volumes which may be referred to as patches. Registration is performed to align the individual patches. An initial alignment of the individual patches may be such that pairs of patches that are to be aligned using the transformation regressor 66 contain similar information. Such initial alignment may be achieved, for example, through controlled synthetic deformation of a reference image to make a floating image; a rigid registration pre-processing step before dividing the image into patches; or if the patches are sufficiently large.

In some circumstances, a patch-wise registration may be more computationally feasible than a full image registration. The patch-wise registration may require less computing resources. In a patch-wise registration method, a full displacement field may be generated through aggregation of patch-level displacement fields.

In some embodiments, the training of the transformation regressor 66 is specific to particular body parts and/or particular image modalities. For example, in one embodiment, the images used to train the transformation regressor 66 are all MR images of brain slices and the transformation regressor 66 is therefore trained to register MR images of brain slices. In other embodiments, the transformation regressor 66 may be trained on images of any body part, for example cardiac images or images of any suitable organ. The transformation regressor 66 may be trained on 2D or 3D images of any modality.

In an example, two transformation regressors were trained on MR brain image slices:

1. A transformation regressor trained using mean squared error alone (similar to that described above with reference to FIG. 2).

2. A transformation regressor trained using mean squared error and discriminator (similar to that described above with reference to FIG. 5).

The transformation regressors were trained to output displacement fields given two input images (reference image and floating image).

Figure 6:
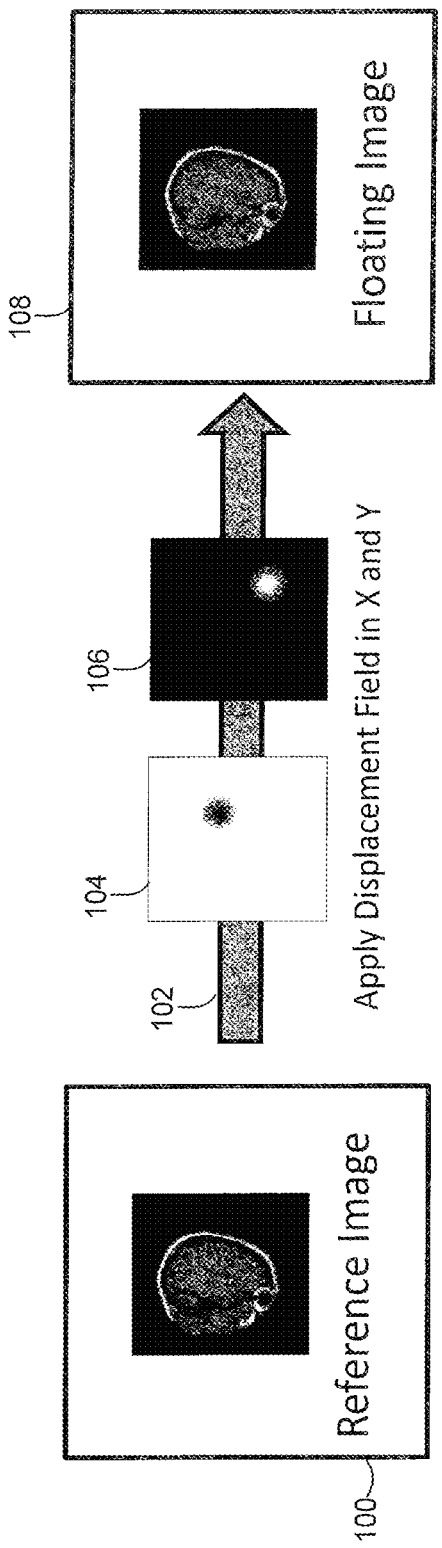
FIG. 6 is a schematic diagram illustrating the application of a predetermined displacement field to a reference image to synthesize a floating image.

FIG. 6 is an illustration of a process of applying a predetermined Gaussian displacement field 104, 106 to a MR brain image slice (reference image 100) to synthesize a floating image 108.

Arrow 102 indicates the process of applying the displacement field 104, 106 to the reference image 100 to obtain the floating image 108. Plots 104, 106 are representations of the displacement field in X and in Y respectively. In plots 104, 106, a color value (shown in the figures in greyscale) represents a degree of deformation. Colors represent the amplitude of the applied warp field. A color value (shown in greyscale) for each pixel in plot 104 represents the amount of X displacement for a corresponding pixel of the image. A color value (shown in greyscale) for each pixel in plot 106 represents the amount of Y displacement for a corresponding pixel of the image.

The results of the comparison of the two trained transformation regressors were as follows:

| | MSE Trained Transformation Regressor | MSE & Discriminator Trained Transformation Regressor |
|---|---|---|
| Peak Signal-to-Noise Ratio (PSNR) between predicted and ground truth displacement fields | 21.64 ± 3.87 | 24.42 ± 5.83 |

It was demonstrated that the transformation regressor that was trained using a combination of mean squared error and a discriminator achieved a higher peak signal-to-noise ratio between predicted and ground truth displacement fields than was achieved by the transformation regressor that was trained using mean squared error alone.

Figure 7:
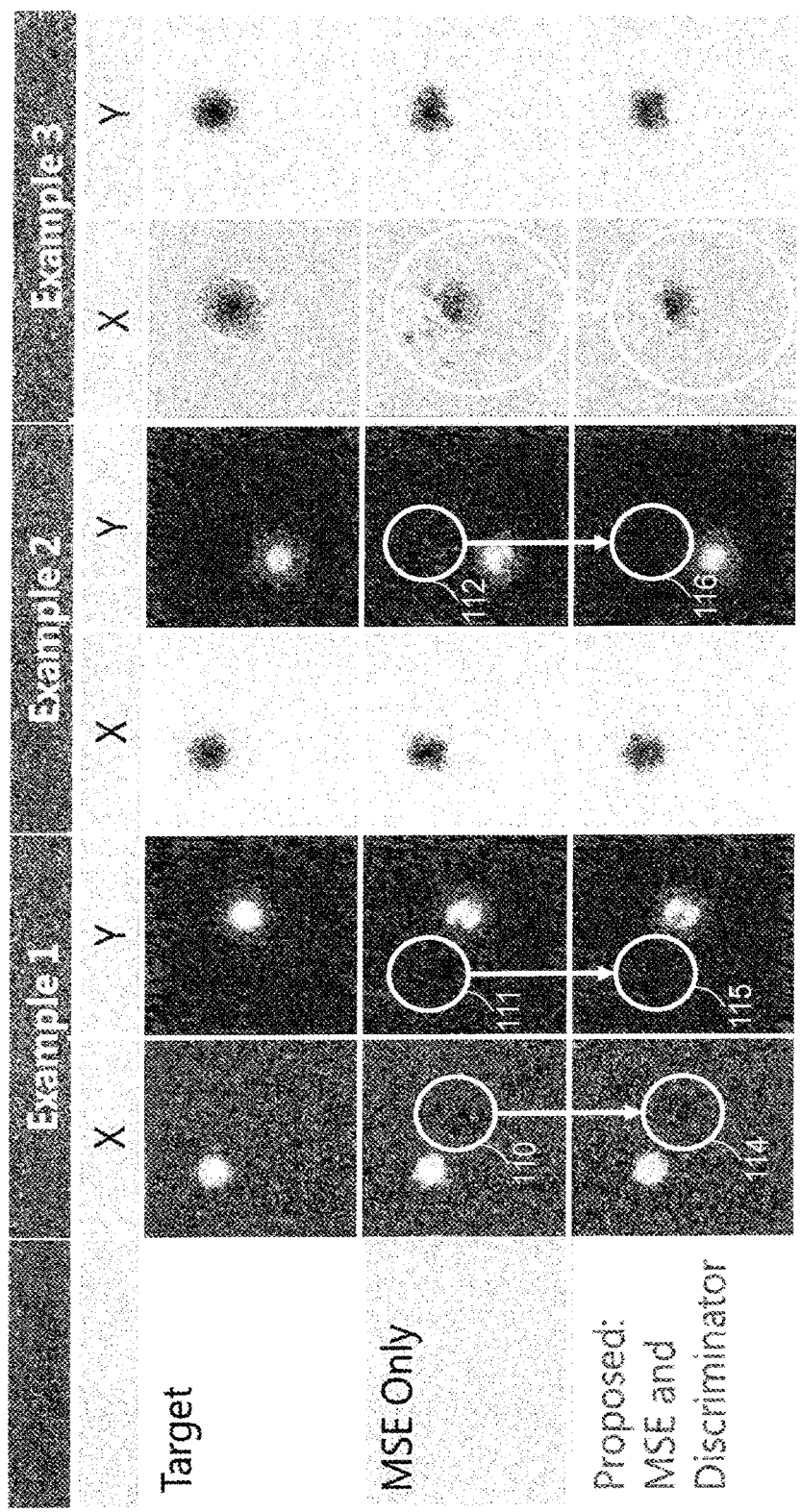
FIG. 7 is a schematic illustration of a series of examples of ground truth displacement fields (top row), displacement fields predicted using a system trained using mean squared error only (middle row), and displacement fields predicted using a system trained using mean squared error and discriminator feedback (bottom row)

FIG. 7 is a table of images showing the effects of discriminator feedback on the training of the transformation regressor. FIG. 7 provides a visual demonstration of ground truth displacement fields; predicted displacement fields from a transformation regressor trained using solely mean squared error; and predicted displacement fields from a transformation regressor trained within a deterministic adversarial network. Results are shown for each of three validation cases (Example 1, Example 2, Example 3).

Synthetic, ground truth displacement fields are shown in the top row of the table. The X and Y displacements are shown for each of the three examples. A degree of displacement is shown as a color (greyscale). The displacement fields shown were applied to MR brain image slices, to create an image pair to be registered.

The middle row of the table shows the displacement fields that were predicted using a system that was trained using mean squared error alone according to a method similar to that described above in relation to FIG. 2.

The bottom row of the table shows displacement fields that were predicted using a system trained using the mean squared error and discriminator feedback according to an adversarial method similar to that described above in relation to FIGS. 4a and 4b.

Circles 110 to 117 highlight visual improvements in the displacement fields between the middle row (mean squared error alone) and the bottom row (adversarial).

The displacement fields in the middle row differ from the ground truth displacement fields shown in the top row. The displacement fields in the middle row exhibit noisy regions shown by circles 110, 111, 112, 113.

Circles 114, 115, 116, 117 in the bottom row indicate regions corresponding to those indicated by circles 110, 111,

112, 113 respectively in the middle row. It may be seen that there is a reduction in noise around these displaced areas. There is also an increased similarity to the ground truth targets shown in the top row.

Using an adversarial component to augment the training of a neural network which regresses the displacement field between two images may result in improved PSNR statistics. Using an adversarial component may result in displacement fields that are more visually satisfying.

The visual results shown in FIG. 7 demonstrate that displacements predicted by a model trained within a DAN framework (the bottom row) appear to have less spurious clutter around the true displacement in both the x and the y component of the displacement field.

The training method described above in relation to FIGS. 4a and 4b uses a single discriminator 76. In further embodiments, multiple discriminators are used in training a transformation regressor.

It is known that, in some circumstances, ensembles of classifiers may provide more accurate predictions than a single classifier. As such, multiple discriminators may be employed for a single transformation regressor to provide adversarial feedback.

In embodiments, multiple discriminators are used, with each discriminator receiving the predicted displacements.

Figure 8:
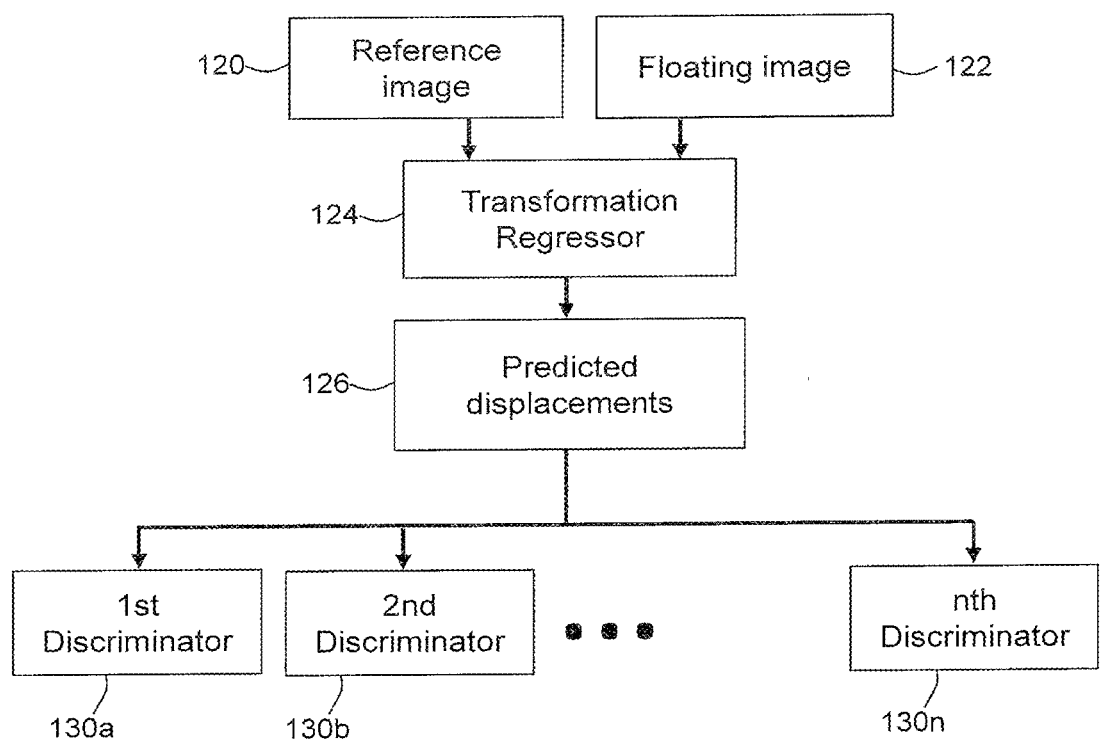
FIG. 8 is a flow chart illustrating in overview a training process using multiple discriminators in accordance with an embodiment.

FIG. 8 is a flow chart illustrating in overview a method according to an embodiment, in which multiple discriminators are used to train the transformation regressor 124.

In training, the training circuitry 24 receives a reference image 120 and floating image 122, which are input to the transformation regressor 124. The transformation regressor 124 outputs a predicted displacement 126.

The predicted displacement 126 is provided to a plurality of discriminators 130a, 130b . . . 130n. Each of the discriminators 130a, 130b . . . 130n outputs a respective determination of whether the displacement provided to it is predetermined or predicted.

In some embodiments, some or all of the discriminators receive other inputs such as the reference and floating image, or some residual image computed between the two, and/or the ground truth displacement, if available.

In some embodiments, each discriminator provides individual adversarial feedback. In other embodiments, a classification from each of the discriminators is aggregated, and the adversarial feedback is derived from the aggregated classifications.

The multiple discriminators may differ from each other in a variety of ways. For example, different ones of the multiple discriminators may be trained on different data. Different ones of the multiple discriminators may have different architectures. Different ones of the multiple discriminators may be initialized using different weights.

Different ones of the multiple discriminators may use different inputs. For example, some discriminators may receive the reference image and floating image (or images or data derived from the reference image and/or floating image) whereas others may not.

In embodiments described above, the discriminator (or each of a plurality of multiple discriminators) comprises a deep learning model. In other embodiments, a discriminator may be used that does not comprise a deep learning model. Any suitable discriminator may be used, as long as the error signal provided by the discriminator is differentiable with respect to the transformation regressor's weights.

In embodiments described above, the discriminator (or each of a plurality of multiple discriminators) is a two-arm discriminator that is configured to receive a predetermined displacement field and a displacement field that is predicted by the transformation regressor, and to output a determination of which of the received displacement fields is the predetermined displacement field and which is the predicted displacement field.

The discriminator has two channels, where one channel receives the output of the transformation regressor and the other channel receives the ground truth displacements.

In other embodiments, the discriminator (or at least one of the multiple discriminators) may comprise a one-arm discriminator that is configured to receive a single displacement field and to output a determination of whether the received displacement field is a predetermined displacement field or a displacement field that is predicted by the transformation regressor. The discriminator has a single channel, where it receives a single set of displacements.

It has been found that in some circumstances a two-arm discriminator may provide a more stable adversarial feedback to the transformation regressor than a one-arm discriminator.

In embodiments described above, the transformation regressor is trained on medical images. The transformation regressor is trained to register first medical image data and second medical image data that are representative of the same anatomical region of a subject, for example images of the same anatomy that are acquired at different times or using different imaging modalities. In other embodiments, the first medical image data is representative of an anatomical region of a subject, and the second medical image data is representative of the anatomical region of the subject or of a corresponding anatomical region of the subject or of a further subject. In some embodiments, one set of medical image data comprises atlas data.

In further embodiments, the transformation regressor may be trained on any type of images (which may or may not be medical images). The transformation regressor may be used to register any type of images. The images may be acquired using any imaging method.

In other embodiments, a method similar to methods described above is used to train a transformation regressor to estimate a depth field for a pair of stereo images. In stereo imaging, two images are acquired from different perspectives using two imaging devices. The difference between the two images is a function of a distance from the two imaging devices to objects represented in the image. By processing the distances between points in the two images, a depth field may be produced that estimates the distance from the imaging devices to the objects in the image.

In some embodiments, pairs of medical images are acquired by first and second imaging devices (for example, first and second cameras) that are offset in position such that the first and second images form a stereo image. The pairs of medical images are input to a transformation regressor, and the transformation regressor is trained to output depth fields for the pairs of medical images. The transformation regressor is trained adversarially with a discriminator to make the predicted depth fields more realistic. A transformation regressor training process in which the transformation regressor is trained to predict depth fields is repeatedly alternated with a discriminator training process in which the discriminator is trained to distinguish between predetermined depth fields and depth fields predicted by the transformation regressor.

In some embodiments, the second imaging device may be the same device as the first imaging device. For example, the position of an imaging device may be moved between acquisition of a first image and acquisition of a second image. In some embodiments, the first imaging device and second imaging device may comprise different parts of a single apparatus, for example different sensors of a single camera.

Features described above with reference to the training and use of a transformation regressor to predict displacement fields may also be applied to the training and use of a transformation regressor to predict depth fields for stereo images.

Certain embodiments provide a method for training a neural network, hereby referred to as the transformation regressor, to estimate non-rigid displacement fields that align two or more images, trained in an adversarial fashion, which consists of minimizing a traditional loss function and maximizing a discriminatory loss.

The transformation regressor may either predict a parametric or a non-parametric transformation to align two or more images. The adversarial training provided by the discriminator may be applied at the whole image level. The adversarial training provided by the discriminator may be applied on a patch-wise basis.

The discriminator may have a single channel, where it receives a single set of displacements. The discriminator may have two channels, where one channel receives the output of the transformation regressor and the other channel receives the ground truth displacements.

The discriminator may additional receive the residual image, or any distance function/similarity metric, between the images input to the neural network regressing the displacement field.

Multiple discriminators may be employed to provide an adversarial/discriminatory loss component for a single given set of displacements.

The images input to the neural network may be of the same modality. The images input to the neural network may be of different modalities.

The traditional loss function may be evaluated between the predicted and ground truth displacements. The traditional loss function may be evaluated between the reference image and the template image distorted with the predicted displacement.

The predicted displacement fields may be used for further registration, segmentation or atlas-based tasks.

The transformation regressor may estimate a depth field for stereo pairs of images.

Methods described above may be applied to any appropriate human or animal anatomy. Methods may be applied to the processing of image data obtained using any appropriate type of imaging procedure, for example any appropriate modality, sequence, acquisition type or processing technique.

Methods are described above with reference to images, for example reference images, floating images and difference image. Operations described above as being performed on images may in practice be performed on sets of image data that are representative of those images. For example, operations may be performed on data comprising sets of pixel or voxel positions and associated intensities. In many cases, operations are performed on image data without the corresponding images being displayed.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus comprising processing circuitry configured to:
receive first image data;
receive second image data; and
apply a transformation regressor to perform a registration process to obtain a predicted displacement that is representative of a transformation between the first image data and the second image data;
wherein the transformation regressor is trained in combination with a discriminator in an adversarial fashion by repeatedly alternating a transformation regressor training process in which the transformation regressor is trained to predict displacements, and a discriminator training process in which the discriminator is trained to distinguish between predetermined displacements and displacements predicted by the transformation regressor.

2. An apparatus according to claim 1, wherein the predicted displacement comprises a predicted displacement field, and the predetermined displacements comprise predetermined displacement fields.

3. An apparatus according to claim 2, wherein the predicted displacement field comprises a non-rigid displacement field.

4. An apparatus according to claim 1, wherein at least one of the transformation regressor and the discriminator comprises a deep neural network.

5. An apparatus according to claim 1, wherein the processing circuitry is further configured to use the predicted displacement in a further process, the further process comprising at least one of a further registration, a subtraction, a segmentation, an atlas-based process, an image fusion, an anatomy detection, a pathology detection.

6. An apparatus according to Claim 1, wherein the transformation is a non-parametric transformation.

7. An apparatus according to Claim 1, wherein the transformation is a parametric transformation.

8. A method comprising:
receiving first image data;
receiving second image data; and
applying a transformation regressor to perform a registration process to obtain a predicted displacement that is representative of a transformation between the first medical image data and the second medical image data;
wherein the transformation regressor is trained in combination with a discriminator in an adversarial fashion by repeatedly alternating a transformation regressor training process in which the transformation regressor is trained to predict displacements, and a discriminator training process in which the discriminator is trained to distinguish between predetermined displacements and displacements predicted by the transformation regressor.

\* \* \* \* \*